United States Patent [19]

Sachdeva et al.

[11] Patent Number: 5,044,947

[45] Date of Patent: Sep. 3, 1991

[54] ORTHODONTIC ARCHWIRE AND METHOD OF MOVING TEETH

[75] Inventors: Rohit C. L. Sachdeva, Plano, Tex.; Shuichi Miyazaki, Ibaraki, Japan; Farrokh Farzin-Nia, Inglewood, Calif.

[73] Assignee: Ormco Corporation, Glendora, Calif.

[21] Appl. No.: 546,559

[22] Filed: Jun. 29, 1990

[51] Int. Cl.$^5$ .............................................. A61C 3/00
[52] U.S. Cl. .......................................... 433/20; 433/18
[58] Field of Search ............................... 433/18, 20, 8

[56] References Cited

U.S. PATENT DOCUMENTS

| | | | |
|---|---|---|---|
| 4,037,324 | 7/1977 | Andreasen | 433/24 |
| 4,144,057 | 3/1979 | Melton et al. | 75/134 |
| 4,197,643 | 4/1980 | Burstone et al. | 433/20 |
| 4,337,090 | 6/1982 | Harrison | 148/402 |
| 4,490,112 | 12/1984 | Tanaka et al. | 433/20 |
| 4,565,589 | 1/1986 | Harrison | 148/402 |

FOREIGN PATENT DOCUMENTS 58-164745 9/1983 Japan .

OTHER PUBLICATIONS

Application of Shape Memory Nickel-Titanium Alloys to Orthodontics-Sachdeva, R. et al.—MRS Int'l Mtg. on Adv. Mats. vol. 9, 1989.
Mechanical Behavior of Shape Memory Ti-Ni-Cu Alloys Saburi, T. et al.—MRS Int'l Mtg. on Adv. Mats. vol. 9, 1989.
Effects of Cu Addition on Mechanical Behavior of Ti-Ni Alloy-Migazaki, S. et al.—MRS Int'l Mtg. on Adv. Mats. vol. 9, 1989.
Electron Microscope Observation of the Early Stages of Thermoeleastic Martensitic Transformation in a Ti-Ni-Cu Alloy-Saburi T.—Journal of Common Metals, 118, 217-226, 1986.
Communication Deformation Behavior of NiTi-Based Alloys Melton et al.—Metallurgical Transactions, vol. 9A, Oct. 1978-1487.
The Structure of NiTiCu Shape Memory Alloys R. H. Bricknell, et al.—Metallurgical Transactions, 696-vol. 10A, Jun. 1979.
Kinetics and Thermodynamics of the Shape-Memory Effect in Martensitic NiTi and $(Ni_{1-x}Cu_x)$Ti Alloys--Mercier, O. et al., J. Appl. Phys. 50(9) Sep. 1979.
In situ Observations of the Nucleation and Growth of the Thermoelastic Martensite in a Ti-Ni-Cu Alloy—Saburi et al., Proceedings of the International Conference on Martensitic Transformations(1986) pp. 671-678 The Japan Institute of Metals.

*Primary Examiner*—John J. Wilson
*Assistant Examiner*—Cindy A. Cherichetti
*Attorney, Agent, or Firm*—Marjama & Pincelli

[57] ABSTRACT

An orthodontic appliance made of a shape memory alloy comprising of a nickel, titanium, and copper composition which is formulated to provide the desired loading and unloading forces to the bracket.

50 Claims, 1 Drawing Sheet

ORTHODONTIC ARCHWIRE AND METHOD OF MOVING TEETH

The present invention relates to an improved orthodontic archwire and system for orthodontic movement of teeth.

BACKGROUND OF THE INVENTION

Traditional systems for the orthodontic movement of teeth have typically consisted of the use of a metal wire that is deformed and bent into a shape so as to provide a load on an orthodontic bracket attached to the tooth so as to move it in a predetermined direction. These metal orthodontic archwires are generally formed of a stainless steel, Co—Cr, or titanium based alloys. Two serious disadvantages with such prior art orthodontic archwires is that they have relatively low shape recovery and the force applied by the wire varies substantially as the tooth moves thus requiring frequent adjustment or replacement by the orthodontist. In order to overcome the disadvantage of such wires, it has been suggested in the prior art the use of a shape memory superelastic alloy material for orthodontic archwires. The advantage of these shape memory superelastic alloy orthodontic archwires is that they are able to apply a substantially constant load during movement of the tooth, thus improving efficiency of the orthodontic procedure. Typically, these superelastic alloys are made of a Ni-Ti alloys. An example of such orthodontic archwires are discussed in U.S. Pat. Nos. 4,037,324 and 4,490,112. A limitation encountered with such prior art-type Ni-Ti alloys archwires is that the amount of force applied by the orthodontic archwire to the orthodontic bracket is relatively low thus requiring longer treatment time. An additional problem encountered with such wires is that initial force necessary to engage the wire with the orthodontic bracket is quite high, thus making it difficult for the orthodontist to apply the archwire to the bracket. A further problem encountered with prior art orthodontic superelastic archwires is the substantially constant load is effective for only a relatively short distance and at a relatively low level of force.

Applicants have discovered that by controlling the composition of the shape memory alloy, the disadvantages of prior art shape memory archwires can be minimized or eliminated.

SUMMARY OF THE INVENTION

In one aspect of the present invention there is provided an orthodontic archwire made of a nickel, titanium, and copper alloy formulated to provide the desired physical and mechanical characteristics.

In another aspect of the present invention there is provided a method of moving teeth using an orthodontic archwire which provides a predetermined maximum loading force and a minimum unloading force.

In still another aspect of the present invention there is provided an orthodontic archwire system which provides a predetermined loading stress and a predetermined minimum unloading stress.

DETAILED DESCRIPTION

Figure 1:
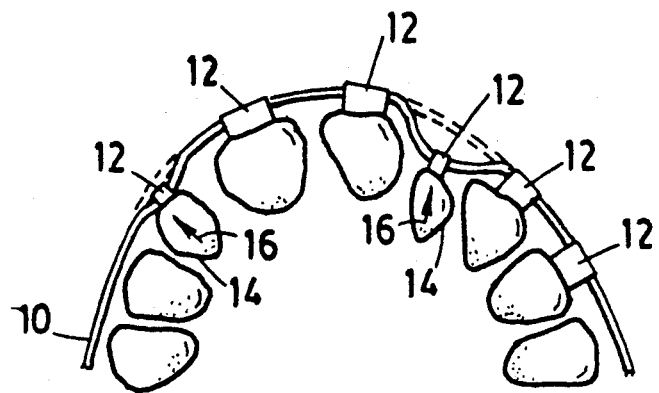
Referring to FIG. 1, there is illustrated a schematic diagram illustrating the principal of orthodontic movement of teeth utilizing a shape memory/superelastic orthodontic archwire made in accordance with the present invention.

Referring to FIG. 1, there is illustrated in schematic form an orthodontic archwire 10 fastened to the teeth of a patient through the use of orthodontic brackets 12 which are bonded to the teeth in any conventional method in the art. For example, but not by way of limitation, the brackets 12 can be bonded directly to each tooth, or welded to a metal band fitted over the tooth. The orthodontic wire is designed to move maloccluded teeth 14 in a predetermined direction (for example, as illustrated by arrow 16) whereby the orthodontic archwire 10 tries to go back to its original formed shape. In the application of the orthodontic wire to the brackets 12 of the maloccluded teeth 14, a certain amount of force (loading force) is required to bend the orthodontic archwire 10 so that it properly engages the orthodontic brackets 12 as illustrated. After the orthodontic wire is securely attached to the orthodontic brackets 12, the unloading force of the orthodontic archwire causes the tooth to move in the desired direction.

Figure 2:
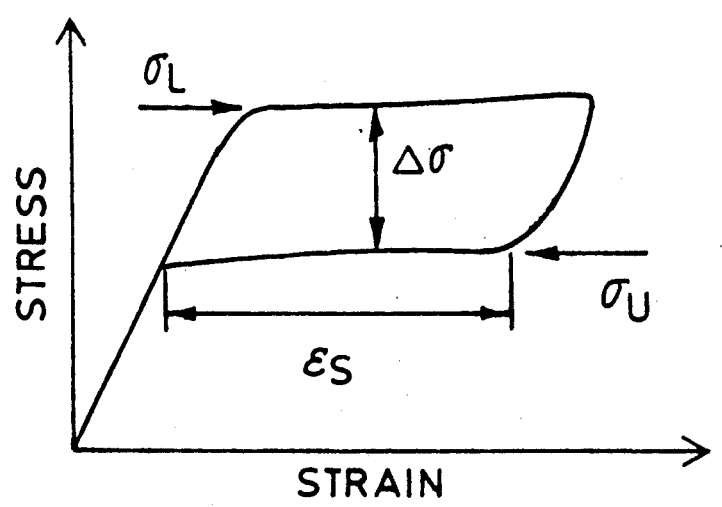
FIG. 2 is a graph illustrating the general stress strain curve for an archwire made of a superelastic shape memory alloy.

Referring to FIG. 2 there is illustrated a typical graph of the stress strain curve for an orthodontic archwire having a nickel titanium alloy composition made in accordance with the prior art, wherein:

$\sigma_L$ = loading stress
$\sigma_U$ = unloading stress
$\Delta\sigma$ = stress hysteresis
$\epsilon_S$ = superelastic stain Values for $\sigma_L$, $\sigma_U$, $\Delta\sigma$ and $\epsilon_S$ were determined for an archwire made of an alloy composition in accordance with the following relationship (Relationship A):

$$Ti_{50-X}Ni_{50+X}$$

Table I below illustrates the results obtained

TABLE I

|  | Col. 1 | Col. 2 | Col. 3 | Col. 4 | Col. 5 |
|---|---|---|---|---|---|
| X | 0 | 0.3 | 0.5 | 0.7 | 1.0 |
| Loading stress ($\sigma_L$) | 400 | 400 | 400 | 400 | 400 |
| Unloading stress ($\sigma_U$) | 75 | 110 | 180 | 190 | 200 |
| Stress hysteresis ($\Delta\sigma$) | 325 | 290 | 220 | 210 | 200 |
| Superelastic strain ($\epsilon_S$) | 4.5 | 4.0 | 3.3 | 2.0 | 0 |

The amount of nickel and titanium was varied by an amount represented by the letter X. Column 1 represents a nickel titanium alloy composition which comprises, by atomic percent, 50% titanium and 50% nickel. Column 2 represents an alloy composition having, by atomic percent, 49.7% titanium and 50.3% nickel. Column 3 represents values for an alloy composition which comprises, by atomic percent, 49.5% titanium and 50.5% nickel. Column 4 represents an alloy composition, by atomic percent, having 49.3% titanium and 50.7% nickel. Column 5 represents an alloy composition which comprises, by atomic percent, 51% titanium and 49% nickel. The high loading stress $\sigma_L$ of approximately 400 Mpa while requires a substantial amount of force to bend the wire so as to attach it properly to the bracket 12, provides a relatively low unloading stress of approximately 75 Mpa to the bracket for the purpose of tooth movement as illustrated by column 1 of Table I.

As the amount of titanium is reduced and nickel increased, as shown by columns 2-5, the distance through which a substantially constant unloading force can be applied to the tooth, as represented by $\epsilon_S$, is reduced such that the alloy of column 5 no longer provides a substantially constant force thus minimizing or eliminating the value of the shape recovery alloy.

Table II below illustrates the stress strain values of an orthodontic archwire 10 made in accordance with the present invention having an alloy composition according to the following relationship (Relationship B) having varying amounts of copper:

$$Ti_{50}Ni_{50-X}Cu_X$$

TABLE II

|  | Col. 1 | Col. 2 | Col. 3 | Col. 4 | Col. 5 | Col. 6 | Col. 7 |
|---|---|---|---|---|---|---|---|
| X | 0 | 1 | 3 | 5 | 10 | 15 | 20 |
| Loading stress ($\sigma_L$) | 400 | 400 | 400 | 400 | 400 | 400 | 400 |
| Unloading stress ($\sigma_U$) | 75 | 70 | 140 | 210 | 290 | 340 | 380 |
| Stress hysteresis ($\Delta\sigma$) | 325 | 330 | 260 | 190 | 110 | 60 | 40 |
| Superelastic strain ($\epsilon_S$) | 4.5 | 4.6 | 4.7 | 4.3 | 2.3 | 1.6 | 1.4 |

Column 1 of Table II is identical to Column 1 of Table I in that this alloy composition has no copper.

Column 1 of Table II illustrates an alloy composition having 1% copper, 50% titanium and 49% nickel (by atomic percent).

Column 2 of Table II illustrates an alloy composition of relationship B having 3% copper. It can be seen that the unloading of this alloy stress was increased to about 140 Mpa, thus increasing the force the orthodontic archwire applies to the bracket 12. It can be further seen that the distance over which a substantially constant force may be applied by the archwire 10 (as represented by $\epsilon_S$) is substantially greater than that the distance over which the alloy composition of column 3 of Table I.

Column 4 of Table II illustrates an alloy composition of relationship B having 5% copper, 50% titantium and 45% nickel. An archwire having this alloy composition provides substantially increased the amount of unloading stress to the orthodontic archwire 10 and has substantially reduced the difference between the loading and unloading stress ($\Delta\sigma$) of the orthodontic archwire to approximately 190 Mpa. Here again, a substantial constant load is applied over a greater distance than the alloy composition of column 3 of Table I.

Column 5 of Table II illustrates orthodontic archwire made in accordance with the present invention having 10% copper. It can be seen that with this alloy composition the unloading stress has been increased to approximately 290 Mpa, thus reducing the difference between loading and unloading stress to approximately 110 Mpa.

By further increasing the amount of copper in the composition to about 15 percent the unloading stress $\sigma_U$ is further increased to approximately 340 Mpa thus further reducing the difference between the loading and unloading stress to approximately 60 Mpa. However, the wire becomes increasingly brittle as more copper is added. Applicants believe that copper percentage greater than about 15% would be too brittle to function effectively as an orthodontic wire.

It can be seen that while the unloading stress can be increased by increasing the amount of copper in the alloy, this is done at the expense of reducing the distance over which the orthodontic archwire applies a substantially constant force. Thus it is important to control the amount of copper in the alloy so that the desired physical and mechanical properties be obtained. The amount of copper in the alloy composition of Relationship B should at least 3% and preferably be in the range of approximately 5% to 11% which will provide an alloy composition having a substantially constant loading/unloading force for a relatively large distance. Preferably the archwire is designed to have a maximum loading stress equal to or less than about 400 Mpa and a minimum unloading stress equal to or greater than about 200 Mpa.

Table III below illustrates stress strain values of a modified orthodontic wire, made in accordance with the present invention. The orthodontic archwire of Table III were made in accordance with the following relationship (Relationship C):

$$Ti_{50-X}Ni_{50}Cu_X$$

TABLE III

|  | Col. 1 | Col. 2 | Col. 3 | Col. 4 | Col. 5 |
|---|---|---|---|---|---|
| X | 0 | 0.3 | 0.5 | 0.7 | 1.0 |
| Loading stress ($\sigma_L$) | 400 | 400 | 400 | 400 | 400 |
| Unloading stress ($\sigma_U$) | 75 | 150 | 230 | 235 | 240 |
| Stress hysteresis ($\Delta\sigma$) | 325 | 250 | 170 | 165 | 160 |
| Superelastic strain ($\epsilon_S$) | 4.5 | 4.0 | 3.4 | 3.3 | 3.2 |

The alloy composition of Relationship C is substantially the same as the composition of Relationship B except that instead of replacing the nickel, with copper, copper replaces the titanium. Column 3 of Table III is identical to columns I of Table and II wherein no copper is present.

Column 3 of Table III illustrates an alloy composition of Relationship C wherein 0.5% copper is present in the alloy. In particular, the alloy composition of column 3 comprises 49.5% titanium, 50% nickel and 0.5% copper. It can be seen that with this alloy the unloading stress was increased to about 230 Mpa while still maintaining a substantially constant superelastic strain $\epsilon_S$ over a fairly large distance. Increasing the amount of copper to 1% and decreases the amount of titanium to 49% provides the values of column 5 of Table III. This alloy composition is very similar to the alloy of column 3. However, here again, the difference between the loading and unloading stresses is relatively small and substantially constant over a relatively large distance.

It can be seen that an orthodontic archwire having an alloy composition as set forth in Relationships B and C can be designed to provide an orthodontic archwire that has lower loading stress while still providing relative high unloading stress for more effective orthodontic movement of teeth, thus delivering more force per tooth movement, and maintains a substantially constant force as the teeth move closer to their intended position.

Applicants have found that the austenitic transformation temperature (Af) of nickel/titanium alloys generally increases with the amount of copper content. The addition of approximately 10% copper in the relationship would increase the austenitic transformation temperature (Af) to approximately 60° C. This temperature is obviously substantially greater than the normal body temperature of 37° C. Thus the potential for activation of this wire becomes extremely small and would only occur when very hot foods are consumed. This type of alloy would only be useful when pulsating loads are desired to be provided to the teeth. In order to provide a substantially constant load, a decrease in the austenitic transformation temperature (Af) is necessary. Applicants have found that the addition of certain other elements will substantially reduce the austenitic transformation temperature to below body temperature of 37° C. For example, the addition of such elements as V, Cr, W, Mn, Fe, Co, and Al have been found to effectively reduce the austenitic transformation temperature of the alloy without substantially affecting its superelastic or shape memory characteristics. It is believed that the addition of 0.5 to 2% iron (Fe) and up to 1.0% chromium (Cr) will reduce the Af temperature of a nickel titanium copper alloy to below body temperature. Depending upon the particular element added and the amount thereof, the transformation temperature may be varied as desired. Applicants believe that in order to provide orthodontic archwires designed to have lower austenitic transformation temperatures that they be made in accordance with the following relationship wherein the amount of the additional element X is no greater than approximately 5%, preferably no greater than about 3%:

$$(Ti_{50-a}/Ni_{50-b}/Cu_{a+b})100-c/X_c$$

wherein:
a = 0-10%,
b = 0-20%,
a+b = 0-20%,
c = 0-5%,
X = V, Cr, Mn, Fe, Mo, Co, W or Al.

While the present invention has been discussed with regard to orthodontic archwires, the alloy composition disclosed herein may be used for other orthodontic appliances such as springs, auxiliaries, loops and brackets.

It is, of course, understood that various other changes may be made without departing from the scope of the present invention, the present invention being limited only by the following claims.

What is claimed:

1. An orthodontic archwire having superelastic properties made of an alloy consisting essentially of nickel, titanium and copper in accordance with the following relationship:

$$Ti_{50}Ni_{50-X}Cu_X$$

wherein X is in the range from about 3-13% (by atomic percent).

2. An orthodontic archwire according to claim 1 wherein X is in the range from about 5-11% (by atomic percent).

3. An orthodontic archwire according to claim 1 wherein X is approximately 10% (by atomic percent).

4. An orthodontic archwire according to claim 1 wherein said archwire produces a maximum loading stress approximately equal to or less than 400 Mpa and a minimum unloading stress equal or greater than about 200 Mpa.

5. An orthodontic archwire according to claim 1 wherein the difference between the loading and unloading stress of said archwire is no greater than about 150 Mpa.

6. An orthodontic archwire according to claim 1 wherein said archwire maintains a substantially constant load during both loading and unloading after reaching the first limit of proportionality.

7. An orthodontic archwire according to claim 1 wherein the archwire includes an additional element selected from the following group: Co, V, Cr, Mn, Fe, Mo, W, Al.

8. An orthodontic archwire according to claim 1 wherein said shape memory alloy has an austenitic transformation temperature (Af) less than or equal to about 37° C. body temperature.

9. An orthodontic archwire according to claim 1 wherein the difference between the maximum and minimum stress for loading and unloading is approximately 110 Mpa.

10. An orthodontic archwire according to claim 1 wherein said orthodontic wire has a minimum unloading stress during unloading of about 200 Mpa.

11. An orthodontic archwire according to claim 1 wherein said archwire has a maximum constant loading stress no greater than about 400 Mpa.

12. An orthodontic archwire according to claim 1 wherein said archwire is made of a material which comprises 35-45% nickel, 50% titanium, about 10% copper, and up to about 5% of said alloy consists of at least one of the following elements: V, Cr, Mn, Fe, Co, Mo, W, or Al.

13. An orthodontic archwire having superelastic properties made of an alloy consisting essentially of nickel, titanium and copper in accordance with the following relationship:

$$Ti_{50-X}Ni_{50}Cu_X$$

wherein X is from about 0.5% to approximately 3.0% (by atomic percent).

14. An orthodontic archwire according to claim 13 wherein X is in the range from about 0.5% to 1.0% (by atomic percent).

15. An orthodontic archwire according to claim 13 wherein X is approximately 1.0% (by atomic percent).

16. An orthodontic archwire according to claim 13 wherein said archwire produces a maximum loading stress approximately equal to or less than 400 Mpa and a minimum unloading stress equal or greater than about 200 Mpa.

17. An orthodontic archwire according to claim 13 wherein the difference between the loading and unloading stress of said archwire is no greater than about 150 Mpa.

18. An orthodontic archwire according to claim 13 wherein an archwire maintains a substantially constant load during both loading and unloading after reaching the first limit of proportionality.

19. An orthodontic archwire according to claim 13 wherein the archwire includes at least one additional element selected from the following group: Co, V, Cr, Mn, Fe, Mo, W, Al.

20. An orthodontic archwire according to claim 13 wherein said transformation temperature of said archwire is less than or equal to about 37° C.

21. An orthodontic archwire according to claim 13 wherein the difference between the maximum and minimum stress load is approximately 110 Mpa.

22. An orthodontic archwire according to claim 13 wherein said orthodontic wire has a minimum load stress during unloading of about 200 Mpa.

23. An orthodontic archwire according to claim 13 wherein said archwire has a maximum loading force no greater than about 375 Mpa.

24. An orthodontic archwire according to claim 13 wherein nickel comprises 40% of said alloy, copper comprises 10% of said alloy, and up to about 3% of said alloy consists of at least one of the following elements: V, Cr, Mn, Fe, Co, Mo, W, or Al.

25. An orthodontic archwire having superelastic properties made of an alloy made in accordance with the following relationship:

$$(Ti_{50-a}/Ni_{50-b}/Cu_{a+b})100-c/X_c$$

wherein:
Ti=nickel
Ni=titanium
Cu=copper
X is selected from the following elements: V, Cr, Mn, Fe, Co, Mo, W, or Al
ranges from:
a=0.0-10%
b=0.0-20%
c=0.0-5%.

26. A method of moving teeth by attaching a plurality of brackets to a plurality of teeth using an orthodontic archwire having superelastic properties such that there is provided second said orthodontic archwire provides a maximum loading stress equal to or less than about 400 Mpa and a minimum unloading stress equal to or greater than about 200 Mpa.

27. A method according to claim 26, wherein the difference between the loading an unloading stress is about 110 Mpa.

28. An orthodontic archwire system comprising of an orthodontic member which undergoes a maximum loading stress equal to or less than about 400 Mpa and a minimum unloading stress equal or greater than about 200 Mpa.

29. An orthodontic archwire system according to claim 28 wherein the difference between the loading and unloading stress is about 110 Mpa.

30. An orthodontic appliance having superelastic properties made of an alloy consisting essentially of nickel, titanium and copper in accordance with the following relationship:

$$Ti_{50}Ni_{50-X}Cu_X$$

wherein X is in the range from about 3-13% (by atomic percent).

31. An orthodontic appliance according to claim 30 wherein X is in the range from about 5-11% (by atomic percent).

32. An orthodontic appliance according to claim 30 wherein said appliance produces a maximum loading stress approximately equal to or less than 400 Mpa and a minimum unloading stress equal or greater than about 200 Mpa.

33. An orthodontic appliance according to claim 30 wherein said appliance maintains a substantially constant load during both loading and unloading after reaching the first limit of proportionality.

34. An orthodontic appliance according to claim 30 wherein the archwire includes an additional element selected from the following group: Co, V, Cr, Mn, Fe, Mo, W, Al.

35. An orthodontic appliance according to claim 30 wherein said shape memory alloy has an austenitic transformation temperature (Af) less than or equal to about 37° C. body temperature.

36. An orthodontic archwire according to claim 30 wherein comprises 35-45% nickel, 50% titanium, about 10% copper, and up to about 5% of said alloy consists of at least one of the following elements: V, Cr, Mn, Fe, Co, Mo, W, or Al.

37. An orthodontic appliance according to claim 30 wherein said appliance is a spring.

38. An orthodontic appliance according to claim 30 wherein said appliance is an auxiliary.

39. An orthodontic appliance according to claim 30 wherein said appliance is a loop.

40. An orthodontic appliance according to claim 30 wherein said appliance is a bracket.

41. An orthodontic appliance having superelastic properties made of an alloy consisting essentially of nickel, titanium and copper in accordance with the following relationship:

$$Ti_{50-X}Ni_{50}Cu_X$$

wherein X is from about 0.5% to approximately 3.0% (by atomic percent).

42. An orthodontic appliance according to claim 41 wherein X is in the range from about 0.5% to 1.0% (by atomic percent).

43. An orthodontic appliance according to claim 41 wherein said appliance produces a maximum loading stress approximately equal to or less than 400 Mpa and a minimum unloading stress equal or greater than about 200 Mpa.

44. An orthodontic appliance according to claim 41 wherein the archwire includes an additional element selected from the following group: Co, V, Cr, Mn, Fe, Mo, W, Al.

45. An orthodontic appliance according to claim 41 wherein said appliance is a spring.

46. An orthodontic appliance according to claim 41 wherein said appliance is an auxiliary.

47. An orthodontic appliance according to claim 41 wherein said appliance is a loop.

48. An orthodontic appliance according to claim 41 wherein said appliance is a bracket.

49. An orthodontic appliance according to claim 41 wherein nickel comprises 40% of said alloy, copper comprises 10% of said alloy, and up to about 3% of said alloy consists of at least one of the following elements: V, Cr, Mn, Fe, Co, Mo, W, or Al.

50. An orthodontic appliance made of a shape memory alloy made in accordance with the following relationship:

$$(Ti_{50-a}/Ni_{50-b}/Cu_{a-b})100-c/X_c$$

wherein:
Ti=nickel
Ni=titanium
Cu=copper
X is selected from the following elements: V, Cr, Mn, Fe, Co, Mo, W, or Al
ranges from:
a=0.0-10%
b=0.0-20%
c=0.0-5%.

* * * * *